(12) United States Patent
Timmermans et al.

(10) Patent No.: US 8,101,798 B2
(45) Date of Patent: Jan. 24, 2012

(54) MANUFACTURE OF SUBSTANTIALLY PURE MONOCHLOROACETIC ACID

(75) Inventors: Roxana Stoenescu Timmermans, Basel (CH); Gerhard Kettenbach, Grenzach-Wyhlen (DE)

(73) Assignee: Buss Chemtech AG (CH)

( * ) Notice: Subject to any disclaimer, the term of this patent is extended or adjusted under 35 U.S.C. 154(b) by 65 days.

(21) Appl. No.: 12/438,664

(22) PCT Filed: Aug. 28, 2007

(86) PCT No.: PCT/EP2007/058908
§ 371 (c)(1),
(2), (4) Date: Feb. 24, 2009

(87) PCT Pub. No.: WO2008/025758
PCT Pub. Date: Mar. 6, 2008

(65) Prior Publication Data
US 2010/0029984 A1   Feb. 4, 2010

(30) Foreign Application Priority Data
Sep. 1, 2006 (EP) .................................. 06018382

(51) Int. Cl.
*C07C 51/00* (2006.01)
*C07B 53/00* (2006.01)
(52) U.S. Cl. ........................................ 562/604; 562/606
(58) Field of Classification Search .................. None
See application file for complete search history.

(56) References Cited

U.S. PATENT DOCUMENTS

| 3,304,325 | A | * | 2/1967 | Foster ........................... 562/604 |
| 3,739,023 | A | | 6/1973 | Sennewald et al. |
| 3,829,478 | A | | 8/1974 | Ohorodnik et al. |
| 5,414,116 | A | * | 5/1995 | Correia ........................ 562/606 |
| 5,475,135 | A | * | 12/1995 | Correia et al. ................ 562/602 |
| 5,756,840 | A | | 5/1998 | Ebmeyer et al. |
| 6,387,345 | B1 | * | 5/2002 | Gestermann et al. ......... 423/502 |
| 2004/0102664 | A1 | * | 5/2004 | Iikubo et al. .................. 570/166 |
| 2005/0090698 | A1 | * | 4/2005 | Merkel et al. ................. 570/155 |
| 2006/0155152 | A1 | * | 7/2006 | Cramers et al. ............... 568/679 |

FOREIGN PATENT DOCUMENTS

DE  1 915 037  10/1970

OTHER PUBLICATIONS

Cramers P et al, "Advanced Hydrogenation Technology for Fine Chemical and Pharmaceutical Applications", Pharmachem, B5, Milan, IT, Jun. 2002, pp. 7-9.
International Search Report and Written Opinion, dated Dec. 6, 2007.

* cited by examiner

*Primary Examiner* — Daniel Sullivan
*Assistant Examiner* — Jennifer C Sawyer
(74) *Attorney, Agent, or Firm* — Hayes Soloway P.C.

(57) ABSTRACT

A process for the manufacture of substantially pure monochloroacetic acid from a liquid chloroacetic acid mixture comprising monochloroacetic acid and dichloroacetic acid, in particular in an amount of 2 to 40 percent by weight, wherein said mixture, further mixed with a suspended hydrogenation catalyst, is mixed with hydrogen gas and the resulting mixture is brought to reaction in a reactor, which is characterized in that the reactor is a loop reactor comprising a gas and liquid recirculation system coupled via an ejector mixing nozzle, in which reactor the gas and liquid are circulated in co-current flow, and the mixing intensity introduced to the liquid phase is at least 50 W/l of liquid phase.

27 Claims, 1 Drawing Sheet

MANUFACTURE OF SUBSTANTIALLY PURE MONOCHLOROACETIC ACID

Figure 1:
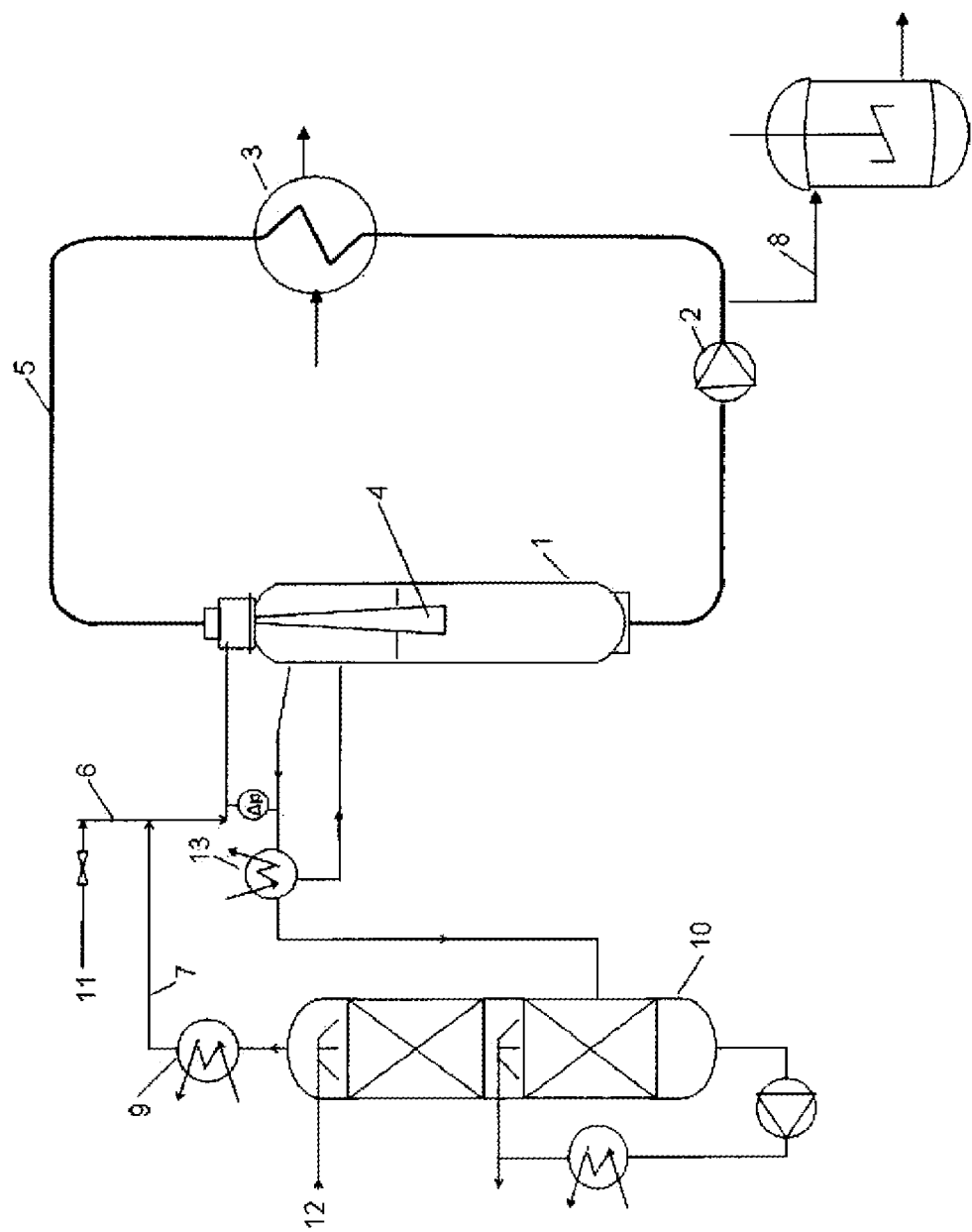

The present invention relates to the manufacture of substantially pure monochloroacetic acid (MCCA), in particular from a liquid mixture comprising monochloroacetic acid and a major quantity of dichloroacetic acid (DCCA), e.g. 2 to 20 percent by weight, and, as the case may be, also trichloroacetic acid.

Monochloroacetic acid is required for the synthesis of many base chemicals, in particular for the pharmaceutical or cosmetic industry. On an industrial scale monochloroacetic acid is usually manufactured by direct chlorination of acetic acid, said reaction, however, resulting unavoidably in a rather crude product only, comprising, in addition to the desired monochloroacetic acid, major amounts of dichloroacetic acid and sometimes trichloroacetic acid as well as residual acetic acid. It has particularly been found to be practically impossible to eliminate the formation of the troublesome by-product dichloroacetic acid. The amount of dichloroacetic acid appearing in the ultimate product varies in general from about 1% to 6% depending upon the specific technique of chlorination applied. In many industrial fields, however, such amounts of impurities are not acceptable for monochloroacetic acid, and it is therefore specified for many applications of monochloroacetic acid that the dichloroacetic acid content of the product must not exceed values of 0.5 percent by weight and frequently even a lower percentage.

The undesirable by-products, in particular the dichloroacetic acid, must therefore normally be removed from the monochloroacetic acid raw product before further use. Whereas acetic acid could be easily removed, e.g. by distillation, it is practically impossible, because of the proximity of the boiling points of monochloroacetic acid (189° C.) and of dichloroacetic acid (194° C.), to separate these species by distillation in a reasonably economic way.

It has therefore been tried to remove the higher chlorinated acetic acids from the main product by recrystallization techniques or by selective catalytic hydrogenation of the crude product.

Recrystallization can decrease the concentration of dichloroacetic acid in the crude product mixture by a factor of about 4 in one single recrystallisation stage, for instance from about 3 percent to about 0.75 percent, so that normally more than one stage is required to meet the usual industry demands (cf. e.g. U.S. Pat. No. 5,756,840). In addition to the requirement of passing a two-stage purification, the recrystallization furthermore ends up in large amounts a mother liquor containing major quantities of monochloroacetic acid and about 18 to 40 percent by weight of dichloroacetic acid which could not economically be worked up so far and thus has generally been discarded as waste.

A conventional process for the hydrogenation (or dechlorination) of a crude mixture of mono-, di- and trichloroacetic acid in the presence of a catalyst suspended in said mixture, thereby selectively reducing the concentration of the higher chlorinated derivatives in said mixture, is described, for instance, in DE-A-1915037. In this process the crude acetic acid mixture is fed to a reactor and a catalyst is suspended therein. Furthermore, excess hydrogen gas is introduced to the reactor from below, and the crude acid mixture, with the hydrogenation catalyst suspended therein, is circulated through a pipe leading from the top region of the reactor to its bottom region in order to get a good mixing of the suspension of the catalyst and the crude acid mixture. Said circulating conduit for the crude acid furthermore comprises an outlet for continuously removing the dechlorinated monochloroacetic acid product which is then separated from acetic acid if present. The outgoing gas comprising the side product hydrogen chloride and excess hydrogen leaves the reactor through a further pipe leading through a washing column wherein the hydrogen chloride gas is separated from the residual hydrogen gas by washing the gas mixture with water, so that the purified residual hydrogen gas can be returned to the reactor. This prior art hydrogenation process, however, has several disadvantages, the major being that a half-way acceptable conversion of dichloroacetic acid to monochloroacetic acid cannot be achieved without adding specific activators to the crude acid mixture which must be soluble in said chloroacetic acids of the mixture. These activators have therefore generally to be removed again from the purified product in order to meet the usual specifications for monochloroacetic acid, thus requiring a further purification step, e.g. a distillation of the monochloroacetic acid. Furthermore and in spite of the activation, a considerable excess of hydrogen gas is taught to be necessary for the reaction. By the way of example, an about hundred fifty fold excess of hydrogen based on the dichloroacetic acid present in the starting mixture is used according to Example 1 of the reference. Notwithstanding of these disadvantages, the degree of purity achievable with a conventional single-stage hydrogenation is still not really satisfactory.

It has therefore also been suggested to combine a catalytic hydrogenation with a subsequent recrystallisation step. By the way of example, U.S. Pat. No. 5,756,840 discloses a process for preparing high quality monochloroacetic acid in presence of a suitable catalyst, by hydrogenation of a mixture of monochloroacetic and dichloroacetic acid in absence of a solvent, followed by subsequent melt crystallization. The hydrogenation is carried out over a fixed bed catalyst in a tube reactor. In an example, the dichloroacetic acid content of a mono-/dichloroacetic acid mixture could be reduced in the hydrogenation stage from about 3.1 percent by weight to 0.04 percent by weight, and in the subsequent recrystallisation stage further to 0.01 percent by weight. Although the process is disclosed to be useful for mixtures containing up to about 50 percent by weight of dichloroacetic acid, such amounts of said impurity require to pass through the hydrogenation stage twice before melt crystallisation, a process which is not economic. In addition, the amount of hydrogen gas applied according to this document is again rather high and according to the examples a 7 to 143 fold hydrogen excess over the stochiometric amount is applied.

It is the object of the present invention to provide a simple remedy for the disadvantages involved with the prior art purification of mixtures of monochloroacetic acid and higher chlorinated acetic acid derivates, in particular the disadvantages mentioned above.

Surprisingly, it has been found that the disadvantages of the prior art processing can be overcome when a loop reactor is used for the selective catalytic hydrogenation of dichloroacetic acid to monochloroacetic acid, which reactor comprises a gas and liquid recirculation system coupled via an ejector mixing nozzle and in which reactor the gas and liquid are circulated in co-current flow, and said mixing nozzle is shaped thus that a mixing intensity of at least 50 W/l of liquid phase can be introduced to the liquid phase.

It has furthermore been found that the use of a loop reactor according to the invention is specifically advantageous for the manufacture of substantially pure monochloroacetic acid from a mixture comprising monochloroacetic acid, dichloroacetic acid, e.g. in an amount of 2 to 40 percent by weight, and optionally trichloroacetic acid.

Accordingly the present invention also relates to a novel process for the manufacture of substantially pure monochloroacetic acid from a liquid mixture comprising monochloroacetic acid and dichloroacetic acid, particularly in an amount of 2 to 40 percent by weight, wherein said chloroacetic acid mixture, further mixed with a suspended hydrogenation catalyst, is mixed with hydrogen gas and the resulting mixture is brought to reaction in a reactor, which process is characterized in that the reactor is a loop reactor comprising a gas and liquid recirculation system coupled via an ejector mixing nozzle, in which reactor the gas and liquid are circulated in co-current flow, and the mixing intensity introduced to the liquid phase is at least 50 W/l of liquid phase.

For the purposes of the present invention the term "substantially pure" is preferably meant to refer to a monochloroacetic acid product comprising less than 0.1 percent by weight (w %) of dichloroacetic acid, more preferably less than 0.05 w %, most preferably less than 0.02 w % of dichloroacetic acid. Preferably, said "substantially pure" monochloroacetic acid is furthermore free from trichloroacetic acid, i.e. the portion of trichloroacetic acid is below the limits of detection.

The loop reactor used according to the present invention is preferably a so-called "Advanced Buss Loop Reactor", like that or similar to that described e.g. in Peter Cramers and Christoph Selinger: "Advanced hydrogenation technology for fine chemical and pharmaceutical applications" PHARMACHEM, June 2002 in which the reactants are recirculated around a loop by means of a pump and reaction occurs at the injection nozzle in the reactor, assuring a very effective gas/liquid/solid mixing. This type of loop reactor optimises and intensifies the dehydrohalogenation process significantly when compared with conventional technologies. To this purpose, said loop reactor comprises a high performance gassing tool as mixer comprising at its upper end a venturi-type nozzle, through which the recirculated acid mixture, optionally together with fresh liquid acid mixture, and comprising the suspended catalyst enters the reactor and which provides a high velocity jet of said fluid mixture that in turn provides suction to the reaction gas in a gas suction chamber, which is connected with the reactor via a gas-liquid ejector and surrounds said nozzle, thus providing for a very intensive mixing of the fluid and the gas.

The mentioned mixing device, which mixes the gas and liquid phase and maintains the catalysts in suspended form, introduces particularly high mixing intensities into the liquid phase, in general at least 50 W/l of liquid phase, preferably from 50 to 2000 W/l of liquid phase, especially from 100 to 500 W/l of liquid phase.

This method of working is an essential reason for the above-recited advantages over conventional hydrogenation processes which employ typical mixing intensities from 0.1 to 10 W/l of liquid phase only.

The advanced loop reactor, useful for the present invention, generally comprises a gas recirculation conduit connecting the headspace of the reactor with the gas suction chamber on top of the reactor. Unreacted hydrogen in the headspace together with hydrogen chloride which is formed during the dehydrohalogenation reaction is circulated around the gas circuit, drawn by the suction of the self-priming nozzle. Accordingly no additional compressor or other gas lifting system is needed in the gas circuit. This ongoing recycling of the gas is one of the reasons for the very efficient exploitation of the feed hydrogen gas according to the present invention, so that the necessity of using of large stoichiometric excesses of hydrogen as known from prior art can be avoided. In general, the molar quantity of hydrogen applied exceeds the molar quantity of dichloroacetic acid (and trichloroacetic acid, if any) by 0 to about 60 percent, preferably by 0 to 10 percent. However, no stoichiometric excess of hydrogen is mandatory according to the present invention.

The hydrogenation process can advantageously be carried out under a pressure of 0 to 10 barg ("bar gauge" corresponding to an absolute pressure of 1 to 11 bar), preferably 0 to 3 barg.

The reaction temperature is preferably from 130 to 170° C., more preferably from 140 to 155° C.

The catalysts used for the process of the invention are preferably noble metals deposited on an inert support. The hydrogenation is e.g. carried out with commercial available heterogeneous noble metal catalysts, preferably with 1-5% palladium or platinum deposited on charcoal, applying a catalyst concentration of 0.05 to 1.00% by weight, preferably 0.1 to 0.4 wt % based on total feed. The catalysts used according to this invention are prepared in a conventional manner.

In a particularly advantageous mode of the invention the spent catalyst is separated from the product after the hydrogenation and re-used in a following batch adding 1 to 10% calculated on the initial amount of catalyst of fresh catalyst. By this practise the overall catalyst consumption of the process is in a low range of 80 to 125 g/ton of crude chloroacetic acid mixture. Additionally it was found, that the mixture of spent catalyst and fresh catalyst shows improved product selectivity, i.e. a lower tendency to over hydrogenation of monochloroacetic acid to acetic acid. A further specific embodiment of the process according to the present invention is therefore a process as described above, wherein the catalyst of a (first) hydrogenation is removed after use, fresh catalyst is added in an amount of 1 to 10 percent of the amount of catalyst initially used for the first hydrogenation, and said mixture of used and fresh catalyst is used for a subsequent hydrogenation, and so on if desired.

The liquid recirculation system belonging to the loop reactor preferably comprises a heat exchanger, in particular a shell and tube heat exchanger for temperature control. This external heat exchanger is e.g. of advantage because its efficacy is not limited by the reactor size as it would be the case of conventionally coils or other heat exchanging surfaces built into the reactor (although these would, in general, also work). Another advantage of an external heat exchanger is that the full heat exchanger surface is available even if the reactor is operated with a reduced volume of liquid only.

In a particularly preferred embodiment of the process of the present invention the gas recirculation system comprises a device for continuously removing HCl gas formed in course of the hydrogenation process from the recirculated gas stream, and returning substantially only the unreacted hydrogen gas to the ejector mixing nozzle of the loop reactor. In this way it is possible to recirculate the hydrogen and simultaneously avoid the adverse effect of the HCL on the hydrogenation. The removal of hydrogen chloride with an absorption column integrated into the gas recirculation line in the loop reactor provides a remarkable benefit to the reaction, because, for equilibrium reasons, it is very advantageous to maintain the hydrogen chloride content in the gas phase at a very low level in order to ensure the best possible performance of the dehydrohalogenation.

The HCl gas is preferably absorbed in water in a conventional absorber column. To this purpose, the gas mixture is preferably lead through one or a series of condensers, in which the gas is cooled down and where entrained organics are condensed and fed back to the autoclave. The cooled gas mixture enters the absorption column, where the content of hydrogen chloride is completely absorbed by water. The purified hydrogen is sucked back into the loop reactor and re-used for the dehydrohalogenation and the organic phase is preferably returned again to the loop reactor. The suction provided by the self-priming nozzle already mentioned above is also sufficient as propelling force for the gas circulation in case that such a hydrogen chloride separation is interposed.

In more specific embodiment of the above process variant, aqueous hydrochloric acid is manufactured as a second useful product in said process. This aqueous hydrochloric acid product can directly be used for many purposes, i.e. is a marketable product without further processing being necessary in general, e.g. without further purification.

According to the invention e.g. a "crude mixture" of monochloroacetic acid, dichloroacetic acid and acetic acid containing 3 to 4 percent by weight of dichloroacetic acid can be hydrogenated under the above mentioned conditions to yield a product comprising 0.02 percent by weight of dichloroacetic acid maximum or also less than that amount. However, as already indicated above, this technology is also fully adapted for the purification by dehalogenation of chloroacetic acid mixtures comprising a much higher percentage of dichloroacetic acid, e.g. a mother liquor from a monochloroacetic acid crystallisation stage, a "residue mixture" comprising monochloroacetic acid, dichloroacetic acid and acetic acid and e.g. containing about 18 to 40 percent by weight of dichloroacetic acid, which can readily be converted to a final mixture containing $\leq 0.02$ percent by weight of dichloroacetic acid in one single hydrogenation step. This is particularly surprising and an important advantage of the present invention compared to known processes, which normally applied at least two hydrogenation stages for converting chloroacetic acid mixtures having comparably high dichloroacetic acid percentages to an industrially usable monochloroacetic acid product.

This high efficacy together with the particularly high selectivity of the hydrogenation process according to the present invention which still increases with the use time of the catalyst makes it possible that the reaction product obtained by a single stage hydrogenation process according to the present invention must generally not be subjected to any further purification steps to meet all usual industrial demand in the purity of monochloroacetic acid.

The process of the present invention can be carried out batchwise as well as continously. Both variants produce qualitatively improved monochloroacetic acid at lower investment and operational costs.

A continuous process according to invention is specifically preferred, e.g. in view of its normally improved productivity. When running the process according to the invention continuously, the liquid recirculation system advantageously comprises an in-line cross flow filter for recovery of the suspended catalyst from the monochloroacetic acid product continuously leaving the reaction system. A suitable cross-flow filter has e.g. a similar shape as a shell and tube heat exchanger, but is equipped with porous sintered metal cartridges. The reaction suspension (acid mixture and catalyst) is circulated through the inside of the filter cartridges and the filtrate is collected on the shell side of this filter. From time to time the filter surface has to be cleaned again from ratained catalyst, e.g. by means of a back-flush procedure.

As already indicated above, the dehydrohalogenation or hydrogenation process according to the present invention is carried out with particular advantage in an advanced ejector loop reactor like the advanced Buss loop reactor, used to perform hydrogenations of liquids in which a heterogeneous catalyst is suspended to form a slurry phase. For further illustration a suitable device is described following with reference to FIG. 1.

The installation comprises an autoclave (1), a reaction pump (2), a heat exchanger for liquid phase (3), a mixing nozzle (4) for sucking and dispersing the hydrogen into the liquid reaction mixture which permanently circulates between the reaction autoclave (1) and the heat exchanger (3) powered by the reaction pump (2). The hydrogen (11) is fed in pressure controlled into the mixing nozzle (1). The gases in the reactor headspace are circulated around the gas circuit, drawn by the suction of the self-priming nozzle. Entrained organics are condensed (13) and fed back in the reactor. The hydrogen chloride formed during the hydrogenation is absorbed within the absorber column (10) using process water (12). The purified hydrogen is sucked back (7) into the reactor and reused. Pure monochloroacetic acid can be removed through conduit (8).

EXAMPLE 1

Hydrogenation of a Mixture Containing 35.0 wt % Dichloroacetic Acid

A loop reactor with a Venturi mixer and additionally equipped with a condenser and an absorption column integrated in the internal gas circuit as shown in the drawing was used. Into the inertised loop reactor with a working volume of 15 liter were introduced 19 kg of a melted mixture containing 35 wt % DCAA and 65 wt % MCAA. The reaction pump was started and 0.032 kg of a commercially available Palladium-catalyst on carbon support (5% Pd on carbon) was added via the catalyst sluice. The integrated HCl absorption system filled with water was started. The reactor was flushed with hydrogen and subsequently the reaction mixture was heated up to 155° C. The loop reactor was pressurized with hydrogen to 3 barg and the hydrogenation was started by opening the pressure controlled hydrogen supply. During the reaction the gaseous headspace of the reactor, consisting mainly of hydrogen chloride and hydrogen is continuously passed through the internal absorber system, where the hydrogen chloride is removed from the hydrogen by absorption and the purified hydrogen is lead back to the reactor. After 200 minutes the uptake of hydrogen decreased and the reaction was continued for further 10 minutes, after which the reactor content was cooled to 70° C. The reactor was depressurised and flushed with nitrogen. In total 1213 Nl hydrogen were consumed. The resulting product was analysed by means of HPLC and the composition was found to be 96.57 wt % MCAA, 0.02 wt % DCAA and 3.41 wt % acetic acid.

EXAMPLE 2

Hydrogenation of a Mixture Containing 3.0 wt % Dichloroacetic Acid

The same reactor as in example 1 was used to hydrogenate a mixture containing 3.0 wt % DCAA, 95.4 wt % MCAA and 1.2 wt % acetic acid. Into the inertised loop reactor were introduced 19 kg of a melted mixture with the mentioned composition. The reaction pump was started and 0.019 kg of a commercially available Palladium-catalyst on carbon support (5% Pd on carbon) was added via the catalyst sluice. The integrated HCl absorption system filled with water was started. The reactor was flushed with hydrogen and subsequently the reaction mixture was heated up to 150° C. The loop reactor was pressurized with hydrogen to 3 barg and the hydrogenation was started by opening the pressure controlled hydrogen supply. During the reaction the gaseous headspace of the reactor, consisting mainly of hydrogen chloride and hydrogen is continuously passed through the internal absorber system, where the hydrogen chloride is removed from the hydrogen by absorption and the purified hydrogen is lead back to the reactor. After 110 minutes the uptake of hydrogen decreased and the reaction was continued for further 10 minutes, after which the reactor content was cooled to 70° C. The reactor was depressurised and flushed with nitrogen. In total only 104 Nl hydrogen were consumed. The resulting product was analysed by means of HPLC and the composition was found to be 97.94 wt % MCAA, 0.01 wt % DCAA and 2.05 wt % acetic acid.

EXAMPLE 3

Hydrogenation Under Atmospheric Conditions of a Mixture Containing 4.0 wt % Dichloroacetic Acid The same reactor as in example 1 was used to hydrogenate a mixture containing 4.0 wt % DCAA, 93.1 wt % MCAA, 2.5 wt % acetic acid and 0.4 wt % water. Into the inertised loop reactor were introduced 19 kg of a melted mixture with the mentioned composition. The reaction pump was started and 0.076 kg of a commercially available Palladium-catalyst on carbon support (5% Pd on carbon) was added via the catalyst sluice. The integrated HCl absorption system filled with water was started. The reactor was flushed with hydrogen and subsequently the reaction mixture was heated up to 145° C. The hydrogenation was started by opening the pressure controlled hydrogen supply. The pressure was held constant between 0-0.2 barg. During the reaction the gaseous headspace of the reactor, consisting mainly of hydrogen chloride and hydrogen is continuously passed through the internal absorber system, where the hydrogen chloride is removed from the hydrogen by absorption and the purified hydrogen is lead back to the reactor. After 170 minutes the uptake of hydrogen decreased and the reaction was continued for further 10 minutes, after which the reactor content was cooled to 70° C. The reactor was flushed with nitrogen. In total only 140 Nl hydrogen were consumed. The resulting product was analysed by means of HPLC and the composition was found to be 97.62 wt % MCAA, 2.33 wt % acetic acid and no residual DCAA (below detection limit).

EXAMPLE 4

Hydrogenation of a Mixture Containing 3.5 wt % Dichloroacetic Acid Using Recycled Catalyst The same reactor as in example 1 was used to hydrogenate a mixture containing 3.5 wt % DCAA, 95.7 wt % MCAA and 0.8 wt % acetic acid. Into the inertised loop reactor were introduced 19 kg of a melted mixture with the mentioned composition. The reaction pump was started and an initial amount of 0.038 kg of a commercially available Palladium-catalyst on carbon support (5% Pd on carbon) was added via the catalyst sluice. The hydrogenation conditions were identical to example 2. After 60 minutes the hydrogenation was stopped and the reactor content was cooled to 70° C. The reactor was depressurised and flushed with nitrogen. The reaction mixture was filtered at 70° C. over a batch filter to separate the precious metal catalyst from the product. The used catalyst was mixed with 19 kg of melted raw material mixture and additionally 1.9 g of fresh catalyst was added. A new hydrogenation was started according to the procedure described above.

The complete cycle of hydrogenation, filtration and reuse of the catalyst was run through 12 times. The selectivity of the catalyst increased with proceeding number of hydrogenation cycles, measurable by lower formation of byproduct acetic acid.

| Cycle | Product composition | | | Reaction time (min) |
|---|---|---|---|---|
| | DCAA (wt %) | MCAA (wt %) | Acetic acid (wt %) | |
| 1 | 0.09 | 97.53 | 2.38 | 60 |
| 8 | 0.07 | 98.80 | 1.14 | 60 |
| 12 | 0.04 | 98.92 | 1.05 | 60 |

The invention claimed is:

1. A process for the selective catalytic hydrogenation of liquid dichloroacetic acid to monochloroacetic acid, wherein the process is conducted in a loop reactor comprising a gas and liquid recirculation system coupled via an ejector mixing nozzle, in which reactor the gas and liquid are circulated in co-current flow, and said mixing nozzle is shaped such that a mixing intensity of at least 50 W/l of liquid phase is introduced to the liquid phase, whereupon the liquid dichloroacetic acid is hydrogenated to monochloroacetic acid, wherein the process comprises continuously removing HCl gas formed in the process from the recirculated gas and returning the unreacted hydrogen gas to the ejector mixing nozzle of the loop reactor.

2. A process for the manufacture of substantially pure monochloroacetic acid from a liquid chloroacetic acid mixture comprising monochloroacetic acid and dichloroacetic acid,
wherein said mixture, further mixed with a suspended hydrogenation catalyst, is mixed with hydrogen gas, and the resulting mixture is brought to reaction in a loop reactor comprising a gas and liquid recirculation system coupled via an ejector mixing nozzle, in which reactor the gas and liquid are circulated in co-current flow and the mixing intensity introduced to the liquid phase is at least 50 W/l of liquid phase, and wherein the process comprises continuously removing HCl gas formed in the process from the recirculated gas and returning the unreacted hydrogen gas to the ejector mixing nozzle of the reactor.

3. The process according to claim 2, wherein the HCl gas is absorbed in water in an absorber column.

4. The process according to claim 2, wherein hydrochloric acid is manufactured as a second product.

5. The process according to claim 2, wherein the consumption of hydrogen gas is in a molar amount exceeding that of dichloroacetic acid by 0 to 60 percent.

6. The process according to claim 2, wherein said liquid recirculation system comprises a heat exchanger.

7. The process according to claim 2, wherein the hydrogenation is carried out under a pressure of 0 to 10 barg.

8. The process according to claim 2, wherein the hydrogenation is carried out at a temperature of 130 to 170° C.

9. The process according to claim 2, wherein the mixing intensity introduced to the liquid phase ranges from 50 to 2000 W/l of liquid phase.

10. The process according to claim 2, wherein the reaction product removed from said loop reactor is not subjected to further purification steps for removing residual dichloroacetic acid.

11. The process according to claim 2, wherein the hydrogenation catalyst is removed after use in said hydrogenation, fresh catalyst is added in an amount of 1 to 10 percent of the amount of catalyst initially used for the first hydrogenation, and said mixture of used and fresh catalyst is used for a further hydrogenation.

12. The process according to claim 2, run as a continuous process.

13. The process according to claim 2, run as a batch process.

14. The process according to claim 2, wherein the liquid recirculation system comprises an in-line cross flow filter for recovery of the suspended catalyst from the monochloroacetic acid product leaving the reaction system, and the process is run continuously.

15. The process according to claim 3, wherein the HCl gas is absorbed in water in an absorber column after the liquid phase carried with the recirculated gas has been removed in condenser device from said recirculated gas to return it to the loop reactor.

16. The process according to claim 3, wherein hydrochloric acid is manufactured as a second product.

17. The process according to claim 5, wherein the molar amount exceeds that of dichloroacetic acid by 0 to 10 percent.

18. The process according to claim 7, wherein the hydrogenation is carried out under a pressure of 0 to 3 barg.

19. The process according to claim 8, wherein the hydrogenation is carried out at a temperature of 140 to 155° C.

20. The process according to claim 9, wherein the mixing intensity introduced to the liquid phase ranges from 100 to 500 W/l.

21. A process according to claim 2, wherein the liquid chloroacetic acid mixture comprises monochloroacetic acid and 2 to 40 percent by weight dichloroacetic acid.

22. The process according to claim 1, wherein the hydrogenation catalyst comprises noble metals deposited on an inert support.

23. The process according to claim 22, wherein the catalyst comprises 1 to 5 percent palladium or platinum deposited on charcoal.

24. The process according to claim 22, wherein a concentration of 0.05 to 1.00 percent by weight of catalyst is applied.

25. The process according to claim 11, wherein the removal of the catalyst after use, the addition of fresh catalyst and the use of said mixture of used and fresh catalyst for a further hydrogenation is consecutively repeated several times.

26. The process of claim 11, wherein the liquid chloroacetic acid mixture comprises monochloroacetic acid and 2 to 40 percent by weight dichloroacetic acid.

27. The process according to claim 2, wherein the hydrogenation catalyst comprises noble metals deposited on an inert support.

* * * * *